United States Patent [19]

Buerstinghaus et al.

[11] Patent Number: 4,670,425
[45] Date of Patent: Jun. 2, 1987

[54] OXIMINOPHOSPHORIC ACID DERIVATIVES AND THEIR USE FOR CONTROLLING PESTS

[75] Inventors: Rainer Buerstinghaus, Heidelberg; Karl Kiehs, Lampertheim; Heinrich Adolphi, Limburgerhof, all of Fed. Rep. of Germany

[73] Assignee: BASF Aktiengesellschaft, Fed. Rep. of Germany

[21] Appl. No.: 859,905

[22] Filed: May 5, 1986

[30] Foreign Application Priority Data

May 7, 1985 [DE] Fed. Rep. of Germany ....... 3516281

[51] Int. Cl.[4] ..................... A01N 57/02; C07F 9/165; C07F 9/40
[52] U.S. Cl. .................................... 514/112; 558/169
[58] Field of Search ......................... 558/168; 514/112

[56] References Cited

U.S. PATENT DOCUMENTS 4,424,215  1/1984  Buerstinghaus et al. ........... 558/168

FOREIGN PATENT DOCUMENTS 0150822  1/1985  European Pat. Off. .

Primary Examiner—Anton H. Sutto
Attorney, Agent, or Firm—Keil & Weinkauf

[57] ABSTRACT

Oximinophosphoric acid derivatives of the formula

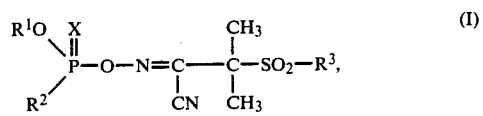

where $R^1$ is straight-chain or branched alkyl of not more than 4 carbon atoms, $R^2$ is a straight-chain or branched alkoxy or alkylthio group of not more than 4 carbon atoms, straight-chain or branched alkyl or not more than 3 carbon atoms, phenyl, amino or a straight-chain alkylamino or dialkylamino radical where alkyl in each case is of not more than 4 carbon atoms, $R^3$ is methyl or ethyl and X is oxygen or sulfur, a process for the manufacture of these oximinophosphoric acid derivatives of the formula I, and their use as pesticides.

7 Claims, No Drawings

OXIMINOPHOSPHORIC ACID DERIVATIVES AND THEIR USE FOR CONTROLLING PESTS

The present invention relates to oximinophosphoric acid derivatives, a process for their preparation, pesticides which contain these phosphoric acid derivatives as active ingredients, and a method of controlling pests with these active ingredients.

Oximinophosphoric acid derivatives are disclosed in German Published Applications Nos. DAS 1,052,981 and DAS 1,238,902 and German Laid-Open Applications Nos. DOS 2,304,848, DOS 2,952,738, DOS 3,135,182 and DOS 3,302,969. They are useful for controlling insects and arachnids. However, their action is not always completely satisfactory, especially at low concentrations.

We have found that oximinophosphoric acid derivatives of the formula I

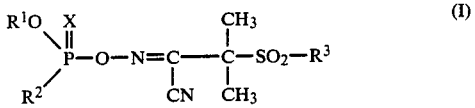

where $R^1$ is straight-chain or branched alkyl of not more than 4 carbon atoms, $R^2$ is a straight-chain or branched alkoxy or alkylthio group of not more than 4 carbon atoms, straight-chain or branched alkyl of not more than 3 carbon atoms, phenyl, amino or a straight-chain alkylamino or dialkylamino radical where alkyl in each case is of not more than 4 carbon atoms, $R^3$ is methyl or ethyl and X is oxygen or sulfur, possess very good insecticidal, acaricidal and nematicidal activity and are superior to known active ingredients having a similar structure or the same direction of action.

In the above general formula, $R^1$ is preferably methyl or ethyl, $R^2$ is preferably methoxy, ethoxy, n-propylthio, isobutylthio, sec.-butylthio or isopropylamino and X is preferably S.

Particularly preferably, when $R^1$ is methyl or ethyl, $R^2$ is methoxy or ethoxy and X is S.

The oximinophosphoric acid derivatives of the formula I can be obtained by reacting an appropriate α-oximinonitrile with an appropriate (thiono)(thiol)phosphoric(phosphonic) ester (amide) halide:

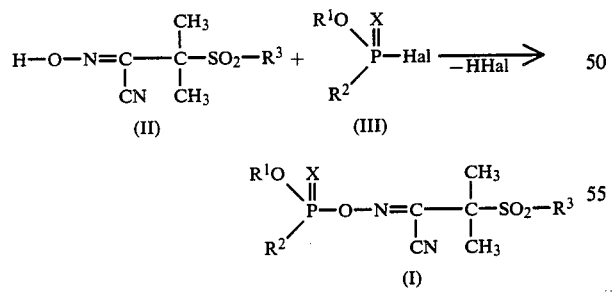

For economic reasons, halogen (Hal) is preferably chlorine.

The reaction is advantageously carried out in a solvent or diluent, examples of suitable substances for this purpose being aliphatic and aromatic hydrocarbons and chlorohydrocarbons such as petroleum ether, benzene, toluene, xylene, gasoline, dichloromethane, chloroform, carbon tetrachloride, 1,2-dichloroethane or chlorobenzene, ethers, such as diethyl ether, di-n-butyl ether, methyl tert.-butyl ether, tetrahydrofuran or dioxane, ketones, eg. acetone, methyl ethyl ketone or methyl isopropyl ketone, and nitriles, such as acetonitrile or propionitrile, as well as mixtures of these substances.

Suitable acid acceptors are the basic agents usually employed for the phosphorylation of hydroxy compounds. Alkali metal carbonates and alkali metal alcoholates, such as sodium carbonate, sodium methylate, sodium ethylate, potassium carbonate, potassium methylate or potassium ethylate, and aliphatic, aromatic and heterocyclic amines, eg. triethylamine, dimethylamine, piperidine, dimethylaniline, dimethylbenzylamine and pyridine, are particularly suitable. In some cases, it is advantageous to use an alkyllithium compound, eg. n-butyllithium, or an alkali metal hydride, eg. sodium hydride.

Instead of adding an acid acceptor, it is also possible to prepare the salts of the α-oximinonitriles (II) for example the alkali metal, alkaline earth metal or ammonium salts, before the reaction, and to react these.

The starting materials are usually reacted in stoichiometric amounts. However, an excess of one or other of the starting materials may be advantageous in specific cases.

The reaction usually takes place at a sufficient rate at above room temperature. In general, the temperature need not exceed 120° C. Since in some cases the reaction takes place with evolution of heat, it may be advantageous to provide a means of cooling.

The active ingredient according to the invention is obtained from the reaction mixture in a conventional manner, for example by adding water, separating the phases and carrying out distillation and/or column chromatography.

The α-oximinonitriles of the formula (II) which are used as starting materials for the preparation of compounds of the formula (I) are novel substances.

However, they can be prepared in a conventional manner (German Published Application DAS No. 1,567,147) by chlorinating the corresponding 2-methyl-2-alkylsulfonylpropionaldoximes of the formula IV (for the synthesis, see J. A. Durden et al., J. Agr. Food Chem. 18 (1970), page 454 et seq.) and reacting the product with sodium cyanide or potassium cyanide, in accordance with the following operation:

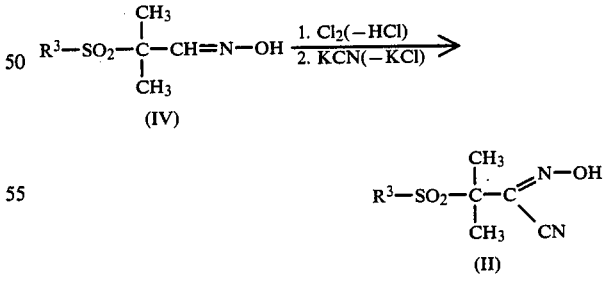

The (thiono)(thiol)phosphoric(phosphonic) ester (amide) halides III furthermore required for the synthesis of the compounds of the formula I are known from Houben-Weyl, Methoden der organischen Chemie, volume XII/2, page 274 et seq. (Stuttgart 1964), and can be prepared by the synthesis routes described there.

Some of the novel compounds of the formula I are obtained in the form of colorless or slightly brownish oils, which can be freed from the final volatile constituents by a prolonged heating at moderately elevated temperatures under reduced pressure (incipient distillation), and can be purified in this manner. Where the compounds of the formula I are crystalline, they can be purified by recrystallization.

Since the compounds of the formula I generally occur as mixtures of structural isomers in the syn and anti forms, their melting or boiling ranges are not very suitable for identification purposes, unless the structural isomers have been separated beforehand. Hence, for each of the substances prepared, results of the elemental analysis and IR spectra with typical absorption maxima from the fingerprint range between 1500 and 800 cm$^{-1}$ are given below.

EXAMPLE 1

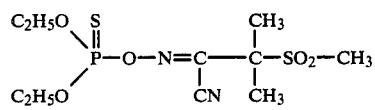

7.22 g of 2-hydroximino-3-methylsulfonyl-3-methylbutyronitrile and 2.7 g of powdered potassium carbonate are dissolved or suspended in 40 ml of acetonitrile, and 7.52 g of O,O-diethylthiophosphoryl chloride are added dropwise, while stirring. The mixture is stirred for 8 hours at 60° C. and then cooled and filtered. The filtrate is evaporated down under reduced pressure, the residue is taken up in ether, and the solution is washed three times with water and freed from the solvent. Incipient distillation at 80° C. and under 0.01 mbar gives 11.6 g of O-(O,O-diethylthiophosphoryl)-2-oximino-3-methylsulfonyl-3-methylbutyronitrile as a virtually colorless, viscous oil.

Yield: 89% of theory.

$C_{10}H_{19}N_2O_5PS_2$ (342); calculated: C 35.1; H 5.6; N 8.2. found: C 35.5; H 5.6; N 8.2.

Infrared absorptions (cm$^{-1}$): 1312, 1163, 1131, 1107, 1021, 947, 904.

Where they are identified by infrared absorptions, the compounds listed in the Table below were likewise obtained by the method described in Example 1; other compounds of the formula (I) can be obtained in a similar manner, with appropriate modification of the methods in accordance with the particular amount required and if necessary after a preliminary experiment to determine the best reaction conditions.

TABLE

| Example No. | $R^1$ | $R^2$ | $R^3$ | X | Infrared absorptions (cm$^{-1}$) |
|---|---|---|---|---|---|
| 2 | $C_2H_5$ | $C_2H_5$ | $CH_3$ | S | 1312, 1131, 1107, 1044, 1014, 947, 897 |
| 3 | $C_2H_5$ | $CH_3$ | $CH_3$ | S | 1311, 1131, 1107, 1034, 957, 912, 892 |
| 4 | $CH_3$ | $OCH_3$ | $CH_3$ | S | 1310, 1131, 1107, 1036, 950, 905 |
| 5 | $C_2H_5$ | S—n-$C_3H_7$ | $CH_3$ | S | 1312, 1131, 1107, 1019, 954, 845, 896 |
| 6 | $C_2H_5$ | $OC_2H_5$ | $CH_3$ | O | 1309, 1165, 1132, 1108, 1032, 943, 909 |
| 7 | $C_2H_5$ | S—sec.-$C_4H_9$ | $CH_3$ | S | 1313, 1131, 1107, 1019, 956, 896 |
| 8 | $C_2H_5$ | NH—i-$C_3H_7$ | $CH_3$ | O | 1312, 1256, 1165, 1130, 1108, 1045, 952, 906 |
| 9 | $C_2H_5$ | $OC_2H_5$ | $C_2H_5$ | S | 1106, 1045, 1022, 947, 904 |
| 10 | $C_2H_5$ | $C_2H_5$ | $C_2H_5$ | S | 1022, 1014, 947, 897 |
| 11 | $C_2H_5$ | $CH_3$ | $C_2H_5$ | S | 1105, 1035, 958, 911, 892 |
| 12 | $CH_3$ | $OCH_3$ | $C_2H_5$ | S | 1106, 1041, 950, 905, 866 |
| 13 | $C_2H_5$ | NH—i-$C_3H_7$ | $C_2H_5$ | O | 1311, 1260, 1128, 1105, 1042, 950 |

PREPARATION OF A TYPICAL INTERMEDIATE

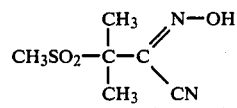

82.5 g of 2-methyl-2-(methylsulfonyl)-propionaldoxime are dissolved in 1.5 l of chloroform, the solution is refluxed and 44.4 g of chlorine gas are passed in. The mixture is kept at the boil for a further hour. After the solvent has been removed, 99.5 g of the corresponding hydroxamic acid chloride remain as a white crystalline mass. 35.7 g of powdered potassium cyanide are suspended in 0.4 l of methanol, and a solution of the above hydroxamic acid chloride in 0.4 l of tetrahydrofuran is added, while cooling with ice. The temperature is kept at from 0° to 5° C. for a further 3 hours, after which the mixture is heated at 35° C. for 1 hour. Potassium chloride is filtered off under suction, the filtrate is evaporated down in a rotary evaporator, and the residue is recrystallized from a 3:1 hexane/ethyl acetate mixture to give 49.5 g (52% of theory) of pure 3-methyl-3-(methylsulfonyl)-2-oximinobutyronitrile as colorless crystals of melting point 139°–141° C.

Infrared absorptions (cm$^{-1}$): 1320, 1282, 1125, 1109, 1028, 1014, 954.

2-Methyl-2-(ethylsulfonyl)-2-oximinobutyronitrile is prepared in a similar manner from 2-methyl-2-(ethylsulfonyl)-propionaldoxime, the product being obtained in a yield of 59% and having a melting point of 123°–125° C.

Infrared absorptions (cm$^{-1}$): 1420, 1294, 1125, 1101, 1020, 741.

The phosphates of the formula I are useful for effectively controlling pests from the class consisting of the insects, arachnids and nematodes. They can be used as pesticides in crop protection, in the hygiene sector, for the protection of stored products and in the veterinary sector.

The active ingredients can be used as such, in the form of their formulations or in the application forms prepared from these, for example in the form of directly sprayable solutions, powders, suspensions or dispersions, emulsions, oil dispersions, pastes, dusts, scattering agents or granules, by spraying, atomizing, dusting, scattering or watering. The application forms depend entirely on the intended uses, but they must ensure as fine a distribution of the active ingredients according to the invention as possible.

The formulations generally contain from 0.1 to 95, and preferably from 0.5 to 90, wt% of active ingredient.

The active ingredient concentration in the ready-to-use formulations may vary within a wide range; generally, it is from 0.0001 to 10, and preferably from 0.01 to 1, %.

The active ingredients may also be used successfully in ultra-low volumes (ULV), it being possible to apply formulations containing more than 95% active ingredient, or even the active ingredient as such, i.e., without additives.

When the active ingredients are used in the open, application rates range from 0.2 to 10, and preferably from 0.5 to 2.0, kg/ha.

Oils of various types, herbicides, fungicides, other pesticides, and bactericides may be added to the active ingredients according to the invention, if desired immediately before use (tankmix). These agents may be added to the agents according to the invention in a weight ratio of from 1:10 to 10:1.

In the following Use Examples the comparative compounds, I, II and III are (O-ethyl-S-n-propyl-dithiophosphoryl)-α-oximino-tetrahydropyran-3-yl-acetonitrile, O-(O-ethyl-methylthio-phosphonyl)-α-cyano-α-(2-methoxymethylprop-2-yl)-acetoxime (Example 2 of U.S. Pat. No. 4,424,215), and (O-ethyl-S-n-propyl-dithio-phosphoryl)-oximino-tetrahydropyran-2-yl)-acetonitrile, respectively.

CONTACT ACTION ON ORIENTAL COCKROACHES (Blatta orientalis)

The bottom of 1 liter preserving jars was treated with an acetonic solution of the active ingredients.

After the solvent had evaporated, 5 adult cockroaches were introduced into each jar.

The kill rate was determined after 48 hours.

| Compound | mg | Kill rate (%) |
|---|---|---|
| Ex. 1 | 0.1 | 100 |
| Ex. 2 | 0.1 | 100 |
| Ex. 3 | 0.1 | 100 |
| Ex. 4 | 0.2 | 100 |
| Ex. 6 | 0.2 | 100 |
| I | 0.4 | 100 |
| II | 0.25 | 100 |

CONTINUOUS CONTACT ACTION ON HOUSEFLIES (Musca demestica)

Petri dishes 10 cm in diameter were lined with 1 ml of acetonic solutions of the active ingredients.

After the solvent had evaporated, 20 4-day old houseflies were placed in each dish.

The kill rate was assessed after 4 hours.

| Compound | mg | Kill rate (%) |
|---|---|---|
| Ex. 1 | 0.01 | 100 |
| Ex. 2 | 0.2 | 100 |
| Ex. 3 | 0.2 | 100 |
| Ex. 5 | 0.2 | 100 |
| Ex. 6 | 0.2 | 100 |
| Ex. 7 | 0.2 | 100 |
| I | 0.2 | 80 |

CONTACT ACTION ON COTTON STAINERS (Dysdercus intermedius)

Petri dishes 10 cm in diameter were lined with 1 ml of acetonic solutions of the active ingredients.

After the solvent had evaporated, 20 larvae of the penultimate stage were placed in each dish and the action was assessed after 24 hours.

| Compound | mg | Kill rate (%) |
|---|---|---|
| Ex. 1 | 0.004 | 100 |
| Ex. 2 | 0.002 | 100 |

-continued

| Compound | mg | Kill rate (%) |
|---|---|---|
| Ex. 3 | 0.004 | 80 |
| Ex. 4 | 0.02 | 100 |
| I | 0.04 | 100 |
| II | 0.05 | 80 |
| III | 0.1 | 100 |

CONTACT ACTION AND THE EFFECT OF INGESTED FOOD ON CATERPILLARS OF THE DIAMONDBACK MOTH (Plutella maculipennis)

Leaves of young cabbage plants were dipped for 3 seconds in aqueous emulsions of the active ingredients; after excess liquid had been briefly allowed to drip off, each leaf was placed on a moist filter paper in a Petri dish. 10 caterpillars of the 4th stage were then put on each leaf.

The action was assessed after 48 hours.

| Compound | mg | Kill rate (%) |
|---|---|---|
| Ex. 1 | 0.004 | 100 |
| Ex. 1 | 0.002 | approx. 80 |
| Ex. 2 | 0.004 | approx. 80 |
| Ex. 3 | 0.004 | approx. 80 |
| I | 0.01 | approx. 80 |
| II | 0.02 | 100 |

CONTACT ACTION ON BEAN APHIDS (Aphis fabae)

Potted bean plants (Vicia faba) exhibiting extensive aphid colonies were sprayed to runoff with aqueous active ingredient formulations.

Assessment took place after 24 hours.

| Compound | Concentration (%) | Kill rate (%) |
|---|---|---|
| Ex. 1 | 0.02 | 100 |
| Ex. 2 | 0.004 | 100 |
| I | 0.1 | 100 |
| II | 0.1 | 60 |

CONTACT ACTION ON TICKS (Ornithodorus moubata)

The experiment was carried out on young ticks which had sucked blood only once. Commercially available tea-bags, each containing 5 animals, were dipped for 5 seconds in the aqueous active ingredient formulation. The bags were then suspended. The temperature was kept at 25° to 26° C. The kill rate was determined after 48 hours.

| Compound | Concentration (%) | Kill rate (%) |
|---|---|---|
| Ex. 1 | 0.001 | 90 |
| Ex. 2 | 0.004 | 100 |
| I | 0.04 | 100 |
|  | 0.02 | 80 |
| II | 0.04 | 100 |
|  | 0.02 | 80 |
| III | 0.04 | 100 |
|  | 0.02 | 80 |

We claim:

1. An oximinophosphoric acid derivative of the formula

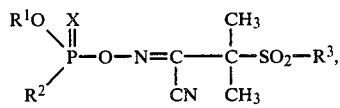 (I)

wherein $R^1$ is straight-chain or branched alkyl of not more than 4 carbon atoms, $R^2$ is a straight-chain or branched alkoxy or the alkylthio group of not more than 4 carbon atoms, straight-chain or branched alkyl of not more than 3 carbon atoms, phenyl, amino or a straight-chain alkylamino or dialkylamino radical where alkyl in each case is of not more than 4 carbon atoms, $R^3$ is methyl or ethyl and X is oxygen or sulfur.

2. A process for combatting pests, wherein an effective amount of the oximinophosphoric acid as set forth in claim 1 is allowed to act on the pests or their habitat.

3. A compound as set forth in claim 2, wherein $R^1$ is ethyl, $R^2$ is ethoxy, $R^3$ is methyl and X is sulfur.

4. A compound as set forth in claim 2, wherein $R^1$ and $R^2$ are each ethyl, $R^3$ is methyl and X is sulfur.

5. A compound as set forth in claim 2, wherein $R^1$ is ethyl, $R^2$ and $R^3$ are each methyl and X is sulfur.

6. A compound as set forth in claim 2, wherein $R^1$ is methyl, $R^2$ is methoxy, $R^3$ is methyl and X is sulfur.

7. A pesticide containing a solid or liquid carrier and a pesticidally effective amount of at least one oximinophosphoric acid derivative of the formula I as set forth in claim 2.

* * * * *